United States Patent [19]

Dragan et al.

[11] Patent Number: 5,306,147
[45] Date of Patent: Apr. 26, 1994

[54] DENTAL SYRINGE AND CARTRIDGE THEREFOR

[76] Inventors: William B. Dragan, 85 Burr St., Easton, Conn. 06612; John Discko, Jr., 50 Laura Rd., Hamden, Conn. 06514

[21] Appl. No.: 82,464

[22] Filed: Jun. 28, 1993

[51] Int. Cl.$^5$ .................................. A61C 5/04
[52] U.S. Cl. .......................................... 433/90
[58] Field of Search ............................ 433/89, 90

[56] References Cited

U.S. PATENT DOCUMENTS

| | | | |
|---|---|---|---|
| 2,206,994 | 7/1940 | Zent | 433/89 |
| 3,595,439 | 7/1971 | Newby et al. | 222/80 |
| 3,827,147 | 8/1974 | Condon | 433/90 |
| 4,330,280 | 5/1982 | Dougherty et al. | 433/90 |
| 4,693,684 | 9/1987 | Blatherwick et al. | 433/90 |
| 5,061,179 | 10/1991 | Dragan | 433/90 |
| 5,125,836 | 6/1992 | Dragan et al. | 433/90 |
| 5,172,807 | 12/1992 | Dragan et al. | 206/219 |

Primary Examiner—John J. Wilson
Attorney, Agent, or Firm—Arthur T. Fattibene; Paul A. Fattibene

[57] ABSTRACT

A dental syringe and disposable capsule for use therewith wherein the disposable capsule includes a body portion formed with a laterally extending collar having a groove therein connected to one end and having a discharge nozzle connected at the other end of the capsule body portion. A displaceable plug seals the material within the cartridge. The syringe includes a plastic barrel having a bore extending therethrough for receiving a reciprocating plunger slidably supported therein. Connected to the barrel adjacent one end is a handle extending normal thereto with a lever pivotally connected relative thereto for engaging the end of the plunger for effecting the displacement of the plunger when the lever is actuated. Connected to the front end of the plastic barrel is a cartridge holder formed as a metal part having a rear portion and a forwardly extending seat portion. The rear portion is embedded into the material of the plastic barrel with the seat portion extending forwardly of the front end of the barrel. The seat portion is defined by an inturned flange spaced forwardly of the front end of the barrel which is notched to define a U-shaped opening. The upper end of the opening is provided with a width sized to the diameter of the groove formed in the collar of the capsule whereby the cartridge is removably retained within the cartridge seat in a simple and expedient manner by placing the collar groove in the notch defined by the inturned flange of the cartridge seat.

10 Claims, 2 Drawing Sheets

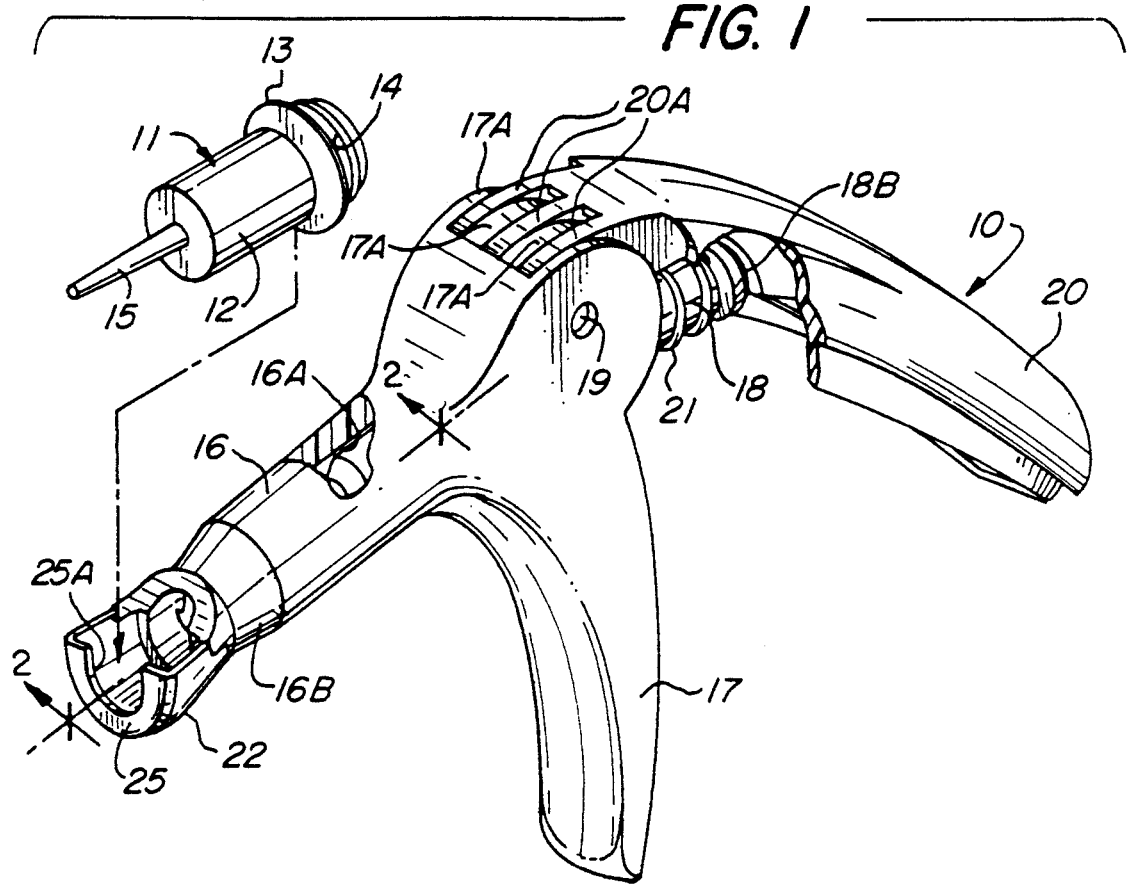
FIG. 1
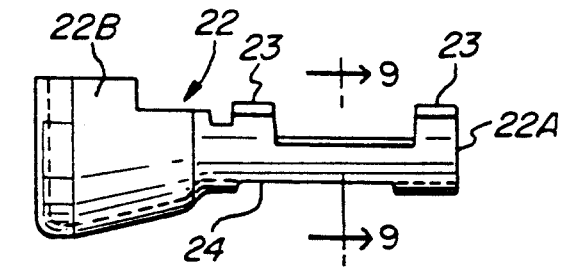
FIG. 6
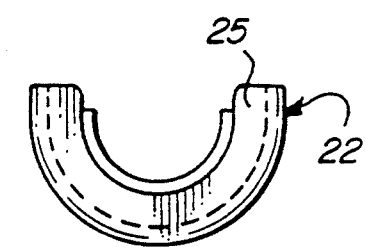
FIG. 8
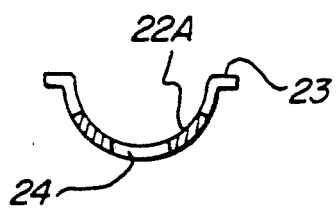
FIG. 7
FIG. 9

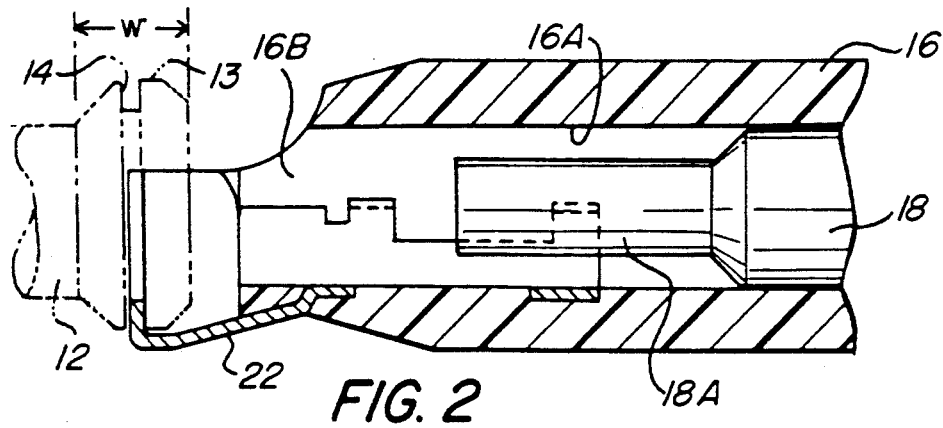
FIG. 2
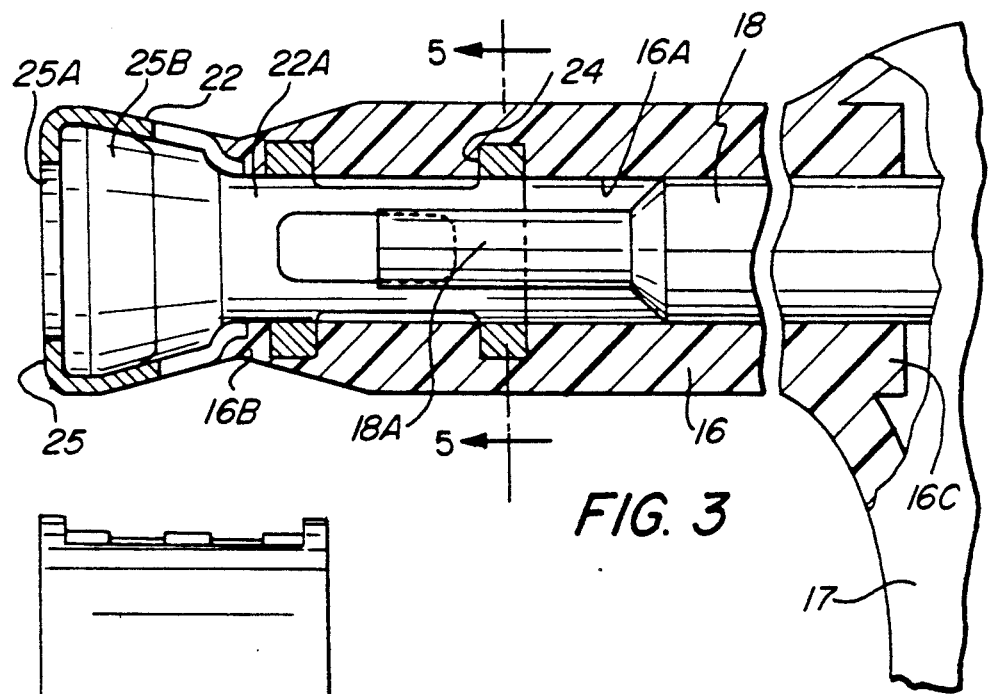
FIG. 3
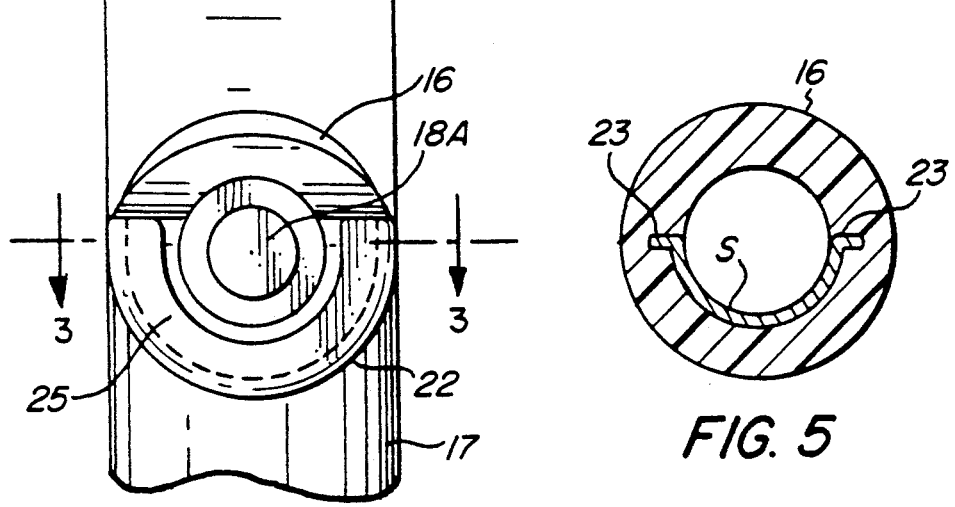
FIG. 4
FIG. 5

DENTAL SYRINGE AND CARTRIDGE THEREFOR

This invention relates to a syringe and cartridge therefor, and more specifically to a dental syringe and dental cartridge adapted to contain various types of dental material utilized in tooth restoration procedures.

PROBLEM AND PRIOR ART

Various types of dental materials are prepackaged in unit dose capsules or cartridges. Single component dental materials such as light activated composite resin material have been prepackaged in unit dose capsules, e.g. of the type disclosed in U.S. Pat. Nos. 3,581,399; 4,963,093; 5,122,057; 4,391,590 and 4,767,326. These patented capsules and others like them are generally characterized as having a cylindrical body portion having a collar or flange circumscribing one end thereof and having an angled discharge nozzle connected to the other end thereof. Such capsules are adapted for use in dental syringes of the type disclosed in U.S. Pat. Nos. 3,581,399; 4,198,756 and 5,125,836. Other variations of such prior known syringes are disclosed in U.S. Pat. Nos. 4,295,828; 4,330,280 and 4,384,853. These syringes are generally characterized as an all plastic syringe having a barrel terminating in a slotted breech opening barrel as disclosed in U.S. Pat. Nos. 4,198,756 or a snap fit slotted breech opening as disclosed in U.S. Pat. No. 4,330,853.

Other dental materials, e.g. multiple component materials which require mixing such as amalgam, glass ionomers and the like, are prepackaged in larger cartridges characterized by a body portion for containing the dental materials in a segregated manner until ready for use. Such cartridges have a laterally extending collar having a circumscribing groove formed intermediate the width of the collar. Such enlarged cartridges are used with an applicator which is formed entirely of metal that utilizes a ratchet type plunger which is incrementally advanced as the handle is actuated to extrude the material disposed within the cartridge. Such applicators are relatively complex and expensive to manufacture.

OBJECT

An object of this invention is to provide for an improved syringe construction which is particularly applicable for use with the mixing cartridges in which multiple component dental materials are prepackaged such as amalgam and glass ionomer type and zinc phosphate materials; and other cements such as carboxylate, zinc oxide and the like; and which is relatively simple in construction and which can be manufactured at substantially less cost than the known amalgam or glass ionomer applicators.

SUMMARY OF THE INVENTION

The foregoing objects and other features and advantages are attained by a syringe construction particularly adapted for use with mixing cartridges containing multiple component dental material that requires mixing prior to use. The syringe construction includes a plastic barrel having a front and rear end and having a handle connected adjacent the rear end of the plastic barrel extending normal to the axis of the barrel. A pivoting lever is operatively disposed relative to the handle and arranged to engage a reciprocating plunger slidably disposed within the bore of the plastic barrel. The lever has a cam or incline that allows the plunger to be fully retracted allowing for easy insertion of the capsule or cartridge without withdrawing the plunger or opening the handle. In accordance with this invention, a metallic cartridge holder having a rear portion and a forwardly extending cartridge seat portion is connected to the front end of the barrel. The rear portion of the cartridge holder defines a cradle which is embedded in the material of the plastic body whereby the inner surface of the cradle becomes a portion of the interior bore of the barrel. The cartridge seat portion extends forwardly of the front end of the plastic barrel and includes an inturned flange spaced forwardly from the front end of the plastic barrel. The inturned flange is provided with a U-shaped notch in which the open end is sized to accommodate the diameter of the groove formed in the cartridge flange. The arrangement is such that the cartridge is removably retained by inserting the groove of the cartridge collar into the notch defined by the inturned flange. Proportioning the width of the groove so as to be slightly greater than the thickness of the inturned flange functions to detachably retain the cartridge within the notch defined by the inturned flange.

IN THE DRAWINGS

FIG. 1 is a perspective exploded view of a dental syringe and disposable cartridge embodying the present invention.

FIG. 2 is a detail sectional side view of the plastic barrel and cartridge holder taken along line 2—2 on FIG. 1 with the cartridge in place.

FIG. 3 is a plan section view of the plastic barrel and cartridge holder taken along line 3—3 on FIG. 4.

FIG. 4 is a fragmentary front end view of the syringe embodying the invention.

FIG. 5 is a sectional view taken along line 5—5 on FIG. 3.

FIG. 6 is a plan view of the cartridge holder detail.

FIG. 7 is a side view of the cartridge holder detail of FIG. 6.

FIG. 8 is a front end view of the cartridge holder detail of FIG. 6.

FIG. 9 is a sectional view taken on line 9—9 of FIG. 7.

DETAILED DESCRIPTION

Referring to the drawings, there is shown in FIG. 1 a dental syringe 10 for use with a dental mixing cartridge 11. The mixing cartridge 11, which is of a conventional construction, comprises essentially a body portion 12 to define a reservoir or chamber for containing the dental material and which is open at one end. Disposed about the body portion 12 adjacent the open end thereof is a laterally extending flange or collar 13. Intermediate the width W of the collar 13 there is provided a groove 14, as best seen in FIG. 2. Connected to the other end of the cartridge body portion is a discharge nozzle 15. Generally, the nozzle 15 is rendered readily flexible so that it can be bent to a suitable working angle, and/or may be formed so as to be angularly disposed relative to the longitudinal axis of the cartridge body portion to provide for a proper working angle. It will be understood that the open end of the body portion 12 is sealed by a displaceable plug.

Such mixing cartridges are generally formed and sized so as to contain two or more components which are maintained in a segregated state until the cartridge is to be used, at which time the cartridge is placed in an agitator to effect the mixing of the material components contained therein. Such cartridges have been used to package various amalgam type dental materials, glass ionomer and other multiple component dental material that require mixing in situ within the cartridges before using. It is also contemplated that such cartridge may also be used to package single component dental material that are best applied by a syringing procedure, e.g. impression materials, composites and the like.

Referring to FIG. 1, there is shown an improved syringe construction which is specifically adapted for use with mixing cartridges 11 of the type described. As shown, the syringe 10 comprises a molded plastic syringe having a plastic barrel 16 which is integrally molded to a handle 17 disposed substantially normal to the axis of the plastic barrel 16. The handle 17 of the syringe in the illustrated embodiment extends beyond or above the axis of the barrel 16 to provide for a pivoting hinge connection as will be hereinafter described, and an additional finger rest.

The barrel 16 is provided with an internal bore 16A that extends through the barrel 16. Accordingly, the barrel has a front end 16B and a rear end 16C that terminates in the handle 17. Reciprocally mounted within the bore 16A of the barrel 16 is a plunger 18. The plunger 18 at its forward end is provided with a reduced ejector portion 18A which is adapted to engage the plug sealing the open end of the cartridge to effect the displacement thereof for extruding the material from the cartridge 11 when the syringe is actuated.

Pivotally connected to the handle 17 about a pivot pin 19 is a lever 20 which extends transversely relative of the plunger 18. As shown, the upper end of the lever 20 is provided with a plurality of spaced leaves 20A that are interleaved with complementary leaves 17A of the handle portion projecting above the barrel. The arrangement is such that the rear end of the plunger 18B is disposed in bearing relationship against the lever 20 so that when the handle 17 and lever are squeezed, the plunger is advanced toward the front end of the barrel 16 to engage the plug of the cartridge 11 to effect the extrusion of the dental material therefrom. A coil spring 21 is disposed about the rear portion of the plunger to impart a spring bias thereto to return the plunger and lever to its inoperative position when the squeezing pressure on the lever 20 is released and to retract the plunger out of the loading area.

In accordance with this invention, a cartridge holder 22 is connected to the front end of the barrel. The cartridge holder 22 comprises a metal stamping formed of a suitable metal, e.g. stainless steel or other rigid metal. The cartridge holder includes a rear portion 22A and a forwardly extending seat portion 22B. As shown, the rear portion 22A is generally semi cylindrical in shape to define a cradle which is adapted to be molded in situ within the front end of the bore 16A of the barrel 16. The rear portion 22A is also provided with opposed laterally extending tabs 23 located adjacent the opposed ends of the rear portion 22A. Also, the bottom of the cradle 22A is provided with an opening 24.

The arrangement is such that the rear portion 22A of the cartridge holder 22 is molded in situ within the front end of the barrel so that the inner surface S of the cradle is coincidental with the internal surface of the bore 16A to provide for a continuous uninterrupted bore. As best seen in FIGS. 2 and 3, the rear portion 22A of the cartridge holder 22 is embedded in the material of the plastic barrel 16. Referring to FIGS. 3 and 5, it will be noted that the laterally projecting tabs 23, which are molded into the plastic material and the flowing the plastic material in the opening 24 of the cradle during the molding of the barrel, provides a firm and integral bonding of the cartridge holder 22 to the front end of the barrel 16.

Projecting forwardly from the front end of the barrel 16 is the cartridge seat portion 22B of the cartridge holder 22. As shown, the forward end of the cartridge seat portion 22B terminates in a front inturned flange 25 which is provided with a U shaped notch 25A which is open at its upper end. In accordance with this invention, the "w" of the notch 25A at its upper end is substantially equal to or slightly greater than the diameter of the groove 14 formed in the collar 13 of the cartridge. The thickness of the inturned flange 25 is slightly less than the width of the groove 14. The arrangement is such that the cartridge 11 is detachably secured simply by inserting the cartridge into the cartridge holder so that the inturned edge of the flange 25 is received within the groove 14 of the cartridge collar 13. As best seen in FIG. 2, the cartridge is securely retained by the cartridge holder 22 in alignment with the bore 16A of the barrel and the plunger 18.

As shown in FIGS. 1, 6 and 7, the seat portion 22B tapers inwardly and upwardly between the front flange 25 and the rear or cradle portion 22A. The spacing between the front flange 25 and the rear portion 22A is sufficient to accommodate the collar portion rearwardly of groove 14 as shown in FIG. 2.

With the cartridge holder described, it will be apparent that the cartridge can be readily inserted and removed therefrom in an expedient and simple manner. The metal cartridge holder 22 molded integral with the barrel 16 also imparts a greater strength to the front end of the barrel. The construction described thus eliminates a point of stress or plastic fatigue resulting in failure or breakage which may occur at the front end of the barrel after a period of continual use previously encountered with syringe barrel assemblies of an all plastic construction.

As the dental syringe described herein is required to be rendered autoclavable to insure against cross-contamination of patients, it is imperative that the coefficient of expansion and contraction between the metallic holder 22 and the plastic barrel 10 be substantially equal so that the mechanical bond between the holder 22 and the barrel 16 can survive repeated autoclaving of the syringe. This is best attained by forming the plastic portion of the syringe 10 of a fully aromatic polyester plastic. One such plastic is a Vectra liquid crystal polymer. The thermal expansion of such plastic between −50 C. to 200 C. has to be noted to be negligible. Autoclaving temperature is approximately 270° F., some 60° F. above boiling, which is well between the range of −50 C. to 200 C.; which renders such plastic readily compatible to the nominal thermal expansion of stainless steel at such autoclaving temperatures.

To prevent pinching, when the lever 20 is squeezed toward the handle 17, a suitable stop means may be provided to limit the movement of the lever relative to the handle. Such stop means may be in the form of aligned complementary abutments 26, 27 projecting from the handle and lever to limit the relative movement therebetween. Thus, when the lever 20 is squeezed, the abutment 27 projecting therefrom engages the abutment 26 of the handle to prevent any complete contact or closing between the adjacent faces of the lever and handle, which may otherwise result in pinching the hand of the operator.

While the invention has been described with respect to the illustrated embodiment, it will be readily understood and appreciated by those skilled in the art that variations and modifications may be made without departing from the spirit or scope of the invention.

What is claimed is:

1. A dental syringe gun for applying a dental material directly to a tooth to be restored comprising
   a plastic barrel having a bore extending therethrough,
   a plunger reciprocally mounted in said barrel,
   said plastic barrel having a front end defining a barrel opening,
   and a cartridge holder connected to said front end in line with said front end opening,
   said cartridge holder comprising a rear portion and a forwardly extending cartridge seat,
   said cartridge seat projecting beyond said front end opening of said barrel,
   said rear portion of said cartridge holder being embedded in the material of said plastic barrel, and
   said cartridge seat being substantially U-shaped terminating in an inturned flange at the forward end thereof,
   said flange having a notch formed with an open end sized to receive the diameter of the cartridge portion adapted to be received therein.

2. A dental syringe gun as defined in claim 1 wherein said cartridge holder is formed of metal.

3. A dental syringe gun as defined in claim 2 wherein said plastic barrel is formed of a material having a coefficient of expansion and contraction comparable to that of the metallic holder.

4. A dental syringe gun as defined in claim 2 wherein said rear portion includes an elongated cradle sized to conform to the interior bore of said barrel,
   said elongated cradle being semi-cylindrical in shape wherein the internal surface of said semi-cylindrical cradle coincides with the internal surface of said bore of said barrel.

5. A dental syringe gun as defined in claim 4, wherein said semi-cylindrical cradle includes oppositely disposed laterally extending tabs embedded in the plastic of said barrel.

6. A dental syringe gun as defined in claim 4 wherein said semi-cylindrical cradle includes an opening formed in the bottom thereof.

7. A dental syringe for applying a dental material to a tooth comprising
   a plastic barrel having a front end and a rear end,
   said barrel having a bore extending therethrough,
   a handle connected to said barrel adjacent the rear end thereof and extending substantially normal to the axis of said barrel,
   a plunger reciprocally mounted in said barrel,
   said plunger extending beyond the rear end of said barrel,
   a lever pivotally mounted for movement relative to said handle portion whereby the end of the plunger extending beyond the rear end of said barrel engages said lever,
   a cartridge holder connected to the front end of said barrel,
   said cartridge holder having a rear portion and a forwardly extending cartridge seat,
   said rear portion of said cartridge holder being embedded in the material of said plastic barrel at the front end thereof,
   said cartridge seat extending forwardly of said front end of said barrel,
   said cartridge seat terminating with an inturned flange at the forward end thereof,
   said flange having a U-shaped notch that is opened at the upper end thereof, and
   said notch having a width at the upper end sized to the diameter of the cartridge portion adapted to be received thereby.

8. A dental syringe as defined in claim 7 wherein said inturned flange is spaced forwardly of the front end of said plastic barrel.

9. In combination, a dental syringe and a disposable cartridge for containing a dental material comprising
   a cartridge including a body portion having a laterally extending collar adjacent one end thereof and a discharge nozzle connected to the other end thereof,
   said collar having a groove disposed about an intermediate portion of said collar,
   and said syringe including a plastic barrel having a forward end and a rear end,
   said barrel having a bore extending therethrough,
   a handle connected to said barrel adjacent the rear end thereof and extending normal to the axis of said barrel,
   a plunger reciprocally mounted in said bore of said barrel,
   said plunger having an end portion extending beyond the rear end of said barrel,
   a lever pivotally mounted relative to said handle,
   said end portion of said plunger being disposed in engagement with said lever,
   a cartridge holder connected to the front end of said barrel,
   said cartridge holder having a rear portion and a forwardly extending cartridge seat,
   said cartridge seat projecting beyond the front end of said plastic barrel,
   and said rear portion being embedded in the material of said plastic barrel,
   said cartridge seat having an inturned flange spaced forwardly of said plastic barrel,
   an open ended notch formed in said flange,
   and said notch having a width at its open end sized to receive the diameter of said groove in said cartridge flange for retaining said cartridge in said cartridge seat.

10. In combination, a dental syringe and a disposable cartridge for containing a dental material as defined in claim 9 wherein said rear portion of said cartridge holder defines a semi-cylindrical cradle wherein the interior surface of said cradle coincides with the surface of said bore,
    laterally extending tabs connected to said cradle, whereby said tabs are embedded in the material of said plastic barrel,
    said cradle having an opening formed in the bottom thereof adapted to be filled with the material of said plastic barrel for securing said cradle to the front end of said barrel.

* * * * *